(12) United States Patent
Crivelli et al.

(10) Patent No.: US 11,169,010 B2
(45) Date of Patent: Nov. 9, 2021

(54) METHOD FOR THE CALIBRATION OF AN IMPLANTABLE SENSOR

(75) Inventors: Rocco Crivelli, Bellinzona (CH); Danillo Roth, St.-Imier (CH); Alec Ginggen, Plymouth, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 0 days.

(21) Appl. No.: 12/509,834

(22) Filed: Jul. 27, 2009

(65) Prior Publication Data

US 2011/0021887 A1    Jan. 27, 2011

(51) Int. Cl.

| | |
|---|---|
| A61B 5/1495 | (2006.01) |
| G01D 11/24 | (2006.01) |
| G01D 18/00 | (2006.01) |
| A61B 5/0215 | (2006.01) |
| G01L 19/08 | (2006.01) |
| A61B 5/00 | (2006.01) |

(Continued)

(52) U.S. Cl.
CPC .......... *G01D 11/245* (2013.01); *A61B 5/0017* (2013.01); *A61B 5/0031* (2013.01); *A61B 5/02154* (2013.01); *A61B 5/02156* (2013.01); *A61B 5/1495* (2013.01); *A61B 5/686* (2013.01); *G01D 5/353* (2013.01); *G01D 18/008* (2013.01); *G01L 19/086* (2013.01); *G01L 19/149* (2013.01)

(58) Field of Classification Search
CPC ................ A61B 5/073; A61B 5/02156; A61B 2560/0223–0238; A61B 5/1495; A61B 5/0017

USPC .............. 600/310, 316, 322, 326, 473, 476, 600/345–365

See application file for complete search history.

(56) References Cited

U.S. PATENT DOCUMENTS

| | | |
|---|---|---|
| 4,206,762 A | 6/1980 | Cosman |
| 4,281,666 A | 8/1981 | Cosman |

(Continued)

FOREIGN PATENT DOCUMENTS

| | | | | |
|---|---|---|---|---|
| EP | 1184351 A1 * | 3/2002 | ............. | C03C 27/08 |
| WO | WO 2008039543 A1 | 4/2008 | | |

OTHER PUBLICATIONS

Tang, Z, et al.; "Data Transmission from an Implantable Biotelemeter by Load-Shift Keying Using Circuit Configuration Modulator," IEEE Transaction on Biomedical Engineering; May 1995; pp. 524-528; vol. 42, No. 5, Gainesville, FL.

(Continued)

*Primary Examiner* — Meredith Weare
(74) *Attorney, Agent, or Firm* — Troutman Pepper Hamilton Sanders LLP

(57) ABSTRACT

An implant includes a processor, RF communication circuitry, optical communication circuitry, a power source and a memory, all of which being hermetically sealed within a housing having a transparent window. Sensor readings are transmitted by RF using the RF communication circuitry to a remote reader after receiving interrogation signals from the reader. During calibration of the sensor, corrective coefficients are calculated by comparing actual sensor pressure readings with known pressure readings. The corrective coefficients are transmitted to the memory of the control circuitry using optical communication wherein modulated light is transmitted through the transparent window of the housing to the photo-detector.

16 Claims, 3 Drawing Sheets

(51) Int. Cl.
    *G01L 19/14*     (2006.01)
    *G01D 5/353*     (2006.01)

(56) References Cited

U.S. PATENT DOCUMENTS

| | | | |
|---|---|---|---|
| 4,281,667 | A | 8/1981 | Cosman |
| 4,385,636 | A | 5/1983 | Cosman |
| 4,705,043 | A * | 11/1987 | Imran .................................. 607/4 |
| 4,944,187 | A * | 7/1990 | Frick et al. ...................... 73/718 |
| 6,049,727 | A * | 4/2000 | Crothall ........................ 600/310 |
| 6,292,697 | B1 * | 9/2001 | Roberts .......................... 607/27 |
| 6,635,014 | B2 | 10/2003 | Starkweather |
| 6,999,685 | B1 * | 2/2006 | Kawase et al. ............... 398/129 |
| 2001/0039437 | A1 | 11/2001 | Taepke |
| 2002/0050925 | A1 | 5/2002 | Arms |
| 2002/0143258 | A1 * | 10/2002 | Weiner et al. ................ 600/476 |
| 2002/0151812 | A1 * | 10/2002 | Scheiner et al. .............. 600/528 |
| 2003/0205090 | A1 * | 11/2003 | Jakobsen ........................ 73/718 |
| 2005/0027175 | A1 * | 2/2005 | Yang .................... A61B 5/0031 |
| | | | 600/302 |
| 2007/0118039 | A1 * | 5/2007 | Bodecker et al. ............ 600/486 |
| 2008/0154101 | A1 * | 6/2008 | Jain et al. ...................... 600/309 |
| 2009/0076353 | A1 | 3/2009 | Carpenter |
| 2010/0090656 | A1 * | 4/2010 | Shearer .............. G06K 19/0707 |
| | | | 320/139 |

OTHER PUBLICATIONS

European Search Report EP10251324.9, dated Jul. 13, 2016.

\* cited by examiner

METHOD FOR THE CALIBRATION OF AN IMPLANTABLE SENSOR

BACKGROUND OF THE INVENTION

1) Field of the Invention

The present invention relates generally to a system and method of calibrating a sensor, and more particularly to a system and method of calibrating a pressure sensor of the type which is located within a hermetically-sealed housing.

2) Discussion of Related Art

Various types of implantable devices exist to measure and record a variety of parameters, such as the pressure, fluid flow, or temperature at a target site within a human body.

The most successful of these implanted devices is the heart pacemaker which not only has helped treat several illnesses associated with the heart, but also has paved the way in developing many technologies that have found widespread use in other implantable systems. These technology developments include low power electronics, wireless telemetry and reliable sensors to interface with biological tissue.

Among the main technological requirements in packaging of implantable microsystem devices are transducer encapsulation (protection) and communication.

Transducer Encapsulation:

One of the most difficult and challenging aspects of implantable devices has been their packaging and encapsulation to not only protect the internal components from the relatively harsh biological environments in which they reside, but to do so while providing a degree of meaningful communication between the internal components and the outside world through the use of a remote reading device.

The sensors located within the implantable devices often include delicate electronics, pneumatics, mechanics and, in some cases optics. Each of these systems are for the most part susceptible to damage by certain conditions found in the testing environment, including excessive moisture or fluids, salts, acids, and high temperatures. When such sensors are implanted within the body of a patient, if not suitably protected, the operative electronics and other delicate components of the sensor (including the supporting components) will quickly become in contact with some hazardous elements. Over time these elements can easily corrode and otherwise degrade the onboard components or the electrical connections, directly affecting the operation and reliability of the particular sensor.

To this end, the sensors that will reside within hazardous environments, including within the body of a human patient, are typically protected within a sealed housing.

Owing mainly to their strength-to-weight ratio, manufacturability, and biocompatibility, titanium, select plastics, stainless steel and glass are common materials used for these housings. The housing sections encapsulate the sensors, supporting circuitry and often a power supply (battery or induction power components) and are hermetically sealed together during manufacture. The housing material is selected for the particular environment it will operate in and for other considerations including intended operative life within that environment, size limitations and cost. Titanium, stainless steel and glass housings are typical for long-term, human-implanted devices because they are proven to effectively protect against harsh environments for long periods of time and are biocompatible.

The process used to hermetically seal the housing sections of an implant depend on the particular material being used. For example, stainless steel and titanium housing sections can be welded together, or brazed or heat-shrunk onto mating parts and later brazed sealed. Glass parts can be brazed and plastic housings can be welded sealed using appropriate ultrasonic welding techniques or an appropriate adhesive that forms a hermetic bond at the interface of the sections.

The response of a particular sensor located within the implant housing strongly depends on the sensor characteristics, but also on the environmental and mechanical conditions seen by the sensor. One problem with using any material for the housing that requires heat to create a hermetic seal (particularly metal or plastic) is that during the heating and subsequent cooling the housing material expands and contracts. This temperature gradient typically changes the volume and pressure within the housing and potentially introduces mechanical stress to any of the delicate onboard sensors. This mechanical stress can cause the sensors to alter their response characteristics. This may be acceptable for some applications, but if the housing contains pressure-measuring sensors, for example, the unpredictable expansion of the housing material and the introduction of mechanical stress will invariably affect the integrity and accuracy of the pressure sensor. For instance, a capacitive pressure sensor uses capacitance to detect slight variations in the plates that make up the capacitor. The sensor is bonded to a base plate. The mechanical stress acting on the plates of the capacitor can influence the way the capacitance changes as a function of the pressure. Any change to the surrounding pressure causes the plates to deform slightly which in turn, changes the capacitance of the capacitor structure. By measuring the slight changes in capacitance, the slight changes in pressure can be calculated. The assembly process of the sensor is one potential source of residual mechanical stress within the sensor. Other physical parameters such as the pressure or the temperature inside the capsule (implanted sensor enclosure) can influence the sensor response.

Glass housings have been found to be more stable during such heating and thereby more appropriate for certain pressure-related applications. If borosilicate glass components are used as the housing, certain sensing components can be directly bonded to a portion of the glass housing well known anodic bonding techniques, wherein an appropriate intermediate material is positioned at the junction of the two parts and extreme heat and a strong electric field are then applied. Owing to the extreme temperatures required during anodic bonding, the glass housing sections are first metalized and then typically bonded to each other using a brazing process that requires much lower temperatures—temperatures that are safe for the internal electronic components. Unfortunately, even these low temperatures and the above-mentioned anodic bonding techniques can often result in residual mechanical stress trapped within the sensor membrane. It is at least for this reason that the implant devices require calibration after the glass housings are hermetically sealed.

In most cases, during the manufacture of a pressure sensor implant (or other types of implant devices), the various parts located adjacent to the sensor, or the sensor structure itself can be affected by the influence of high temperatures. For at least this reason, after the housing is hermetically sealed, the entrapped transducer and associated components must be calibrated by generating a data-set between measured values read by the transducer output and actual known values for a select input.

Communication and Control:

An important consideration in the development of a successful implant device is how the isolated device communicates with the outside world. The packaging required to contain implanted micro-electronic and mechanical devices is different from the packaging used in housing conventional micro electronic components. This is because implant devices by their nature require some level of interaction with their surrounding environment. As a result, the implant device cannot be completely isolated from its surroundings. Selective access needs to be provided to at least the sensing or actuation component of the implant.

One method to achieve this access or communication is through the use of so-called feed-throughs (also called: wire-ports and electrical vias). A feed-through is a bore formed within an otherwise hermetically sealed housing that provides direct access of appropriate electrical conduits to circuitry within the housing. The wiring can be used as a power feed should a remote power supply be used, communication for reading a sensor output, or as a means to calibrate the sensors within the device during manufacturing after the housing is otherwise hermetically sealed. Unfortunately, although the communication link offered by this direct-connect method is usually very effective, it has been proven very difficult to provide a reliable and effective seal within the bore around the electrical conduit. Before the useful life of the implant has been reached, the bore is a common point of a breach-failure of the entire implant. Owing to these sealing difficulties, use of such feed-throughs is preferably avoided entirely.

For at least this reason, conventional implant devices typically operate as independently as possible. The implant will preferably contain its own internal power supply (or will derive its power from a received RF energy signal through RF inductive coupling) and will communicate with the outside world using appropriate wireless telemetry, such as radio frequency (RF).

Unfortunately, providing two-way wireless communication between a remote reader and an implanted device requires telemetry circuitry that is relatively expensive, consumes additional power and takes up precious real estate within the housing. This additional telemetric circuitry is particularly wasteful since two-way communication between a reader and the implant is only required during initial calibration of the implant device shortly after the implant housing sections are hermetically sealed together during its manufacture. A passive implantable pressure sensor, for instance, is interrogated by an external reader. The RF signal powers the device, as mentioned above, but data communication is only made one-way between the implant and the reader, no data needs to flow from the reader to the implant. Once the conventional implant device is calibrated and surgically implanted within a patient, several components of the convention two-way telemetry circuit are no longer used and forever remain within the device as "dead components", taking up volume and continuing to consume, measurable, albeit small amounts of limited on-board power.

OBJECTS OF THE INVENTION

It is therefore an object of the present invention to provide an implant that overcomes the deficiencies of the prior art.

It is another object of the invention to provide a calibration protocol for implantable devices that requires relatively inexpensive and few components to remain within the implant after implantation.

It is yet another object of the invention to provide an implant device that allows for effective two-way communication during initial calibration and which requires inexpensive and few components.

SUMMARY OF THE INVENTION

An implant includes a processor, RF communication circuitry, optical communication circuitry including a photodetector, such as a photodiode or phototransistor, a power source and a memory, all of which being hermetically sealed within a housing having a transparent window or including a transparent part, such as glass. Sensor readings are transmitted by RF using the RF communication circuitry to a remote reader after receiving interrogation signals from the reader. During a calibration process of the sensor, corrective coefficients are calculated using a computer by comparing actual sensor pressure readings with known pressure readings. The corrective coefficients are then transmitted to the memory of the onboard control circuitry using optical communication wherein modulated light is transmitted through the transparent window or part of the housing to the photodetector. Thereafter, any pressure sensor readings within the implant are automatically adjusted using the corrective coefficients located within the memory before being transmitted to a remote RF reader.

The accompanying drawings show examples of embodiments of the present invention. They illustrate how the invention achieves the above stated advantages and objectives.

DETAILED DESCRIPTION OF THE PREFERRED EMBODIMENT

Figure 1:
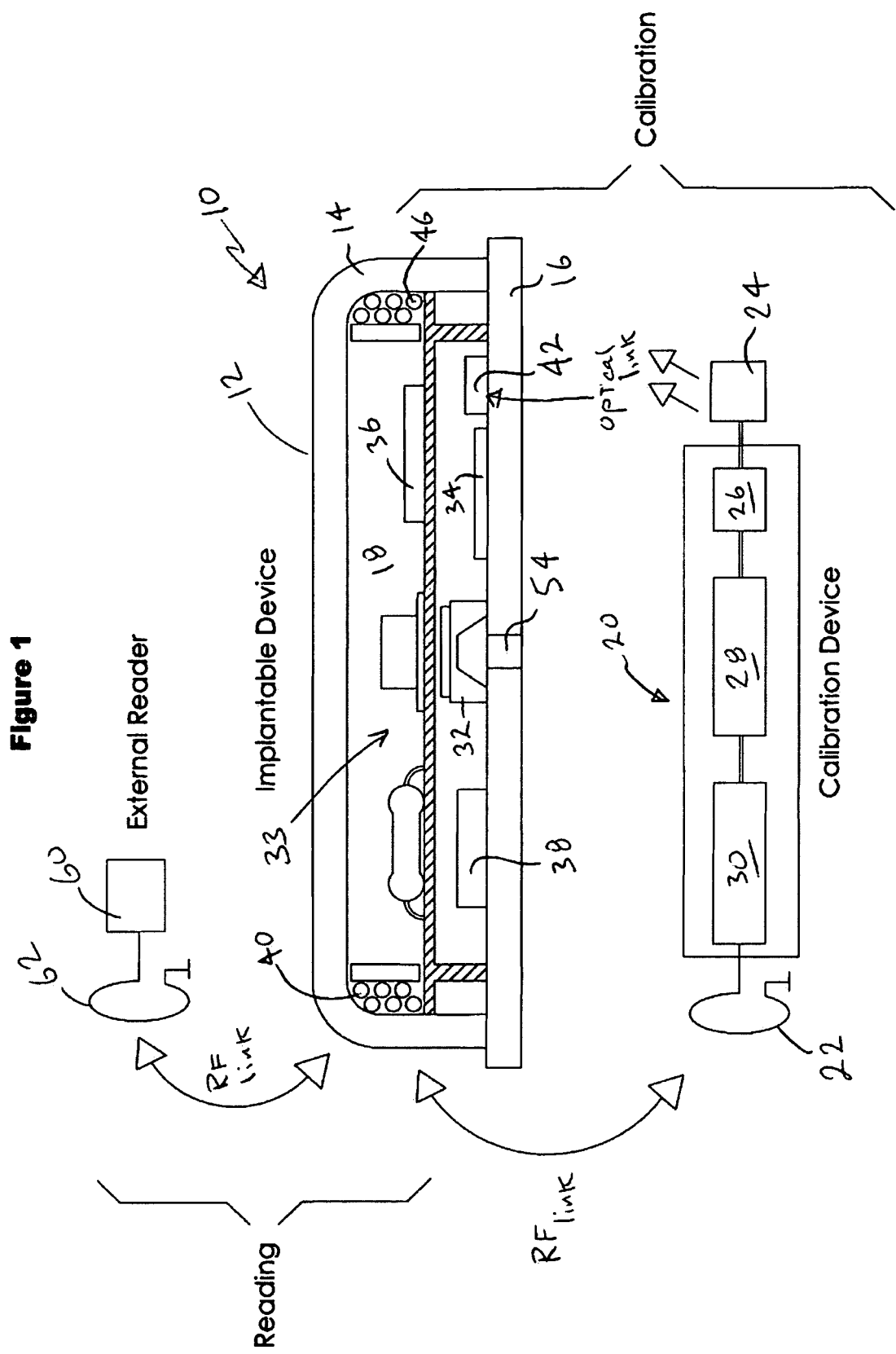
FIG. 1 is a sectional side view of an exemplary implant device and an adjacent schematic representing a calibration system used to calibrate the implant device according to the present invention.

By way of overview and introduction, the present invention relates to the calibration of devices that are implanted into human patients for the purpose of measuring parameters at a particular site within the body. These implanted devices are designed to transmit this information to a remote reader when the implanted device is interrogated by the reader. As mentioned above, such sensors must be hermetically sealed within a housing and that the relatively high temperatures typically incurred during manufacturing can alter the performance and response characteristics of the on-board sensors and the delicate supporting components. To this end, after the sensors and electrical supporting components of the implant device are sealed and become physically inaccessible, they must then be calibrated so that their unique response characteristics become understood and that their resulting readings remain accurate and meaningful.

Calibration is the process of establishing a corrective relationship between the signal output of a measuring device, such as a pressure sensor located within an implant device, and the value of a physical standard having known and accepted response characteristics relating to, for example pressure, flow of a fluid, or temperature. This process, which is typically performed during the manufacture of the implant device results in a set of calibration coefficients (or corrective data) that is unique to each individual sensor being calibrated. This set of calibration coefficients is generally stored in electronic memory located within the implant and is used at prescribed times during the operation of the sensor. Upon interrogation of the implanted sensor (for instance using radio frequency by means of an external reader), the implant electronics will automatically calculate a corrected value of the signal output of the sensor (sensor response) by associating the raw measurement value read by the sensor with the corrective data stored in the implant.

During conventional manufacture and after encapsulation of the implant, the encapsulated sensor is calibrated, typically using the following steps:

A) The non-calibrated encapsulated sensor is "characterized", wherein the implant (with its encapsulated sensor) is placed within a pressure-controlled and temperature-controlled hermetic chamber.

B) The implant is then interrogated wirelessly by a remote control unit.

C) The pressure (P-ref) and temperature (T-ref) within the chamber are varied in a controlled and known manner. The onboard sensor response is continuously read as a function of the changing T-ref and P-ref and recorded during the process.

The output of this characterization step is Sensor-Raw-Data (data from the non-calibrated sensor), where Sensor-Raw-Data is a function of the pressure and temperature of the chamber for each reading:

Sensor-Raw-Data=$f$(P-ref,T-ref).

D) The implant uses an RF link to transmit the sensor-raw data to the remote controller.

E) A computer based algorithm within the remote controller uses this information to compute the sensor calibration coefficients from function (f).

F) The computer uses RF communication to transmit the calculated calibration coefficients to the onboard circuitry in the implant, which are then stored within the onboard non-volatile memory located within the implant.

At this point forward, if the implant is interrogated within an environment having a particular pressure and temperature, the onboard sensor output will automatically be adjusted by the calibration coefficients from the memory so that the signal transmitted back to the remote reader is an accurate (calibrated) reading of pressure Calibrated-Sensor-Output=g(p, T), where function g is the calibrated f function. With the help of this electronically stored calibrated coefficient data, the reader will only receive corrected data from the implant.

Example 1

A pressure sensor is being calibrated in a pressure chamber. Known pressures and temperatures are applied to the chamber while the output signal of the sensor is read at different pressure values. The output signal of the sensor and the known pressure and temperature values within the chamber are compared at different pressures and the difference between the two values if any is noted.

As illustrated in the table below, during the calibration process of a specific sensor, it is determined that the sensor outputs a pressure value of 0.4 PSI when the known pressure is 0.5 PSI. And at a known pressure value of 0.54 PSI, the sensor's reading is just 0.5 PSI. At 0.6 PSI from the sensor, the known pressure value within the chamber is 0.58 PSI. From these three simple data points, a corrective coefficient data set can be generated for this particular sensor so that after the sensor is operational within any environment, a reading from the sensor of 0.4 PSI, for example will automatically be adjusted by adding 0.1 PSI to arrive at a "corrected" and accepted value.

| Sensor Output (PSI) | Actual Measurement (PSI) | Correction factor (PSI) |
|---|---|---|
| 0.4 | 0.5 | +0.1 |
| 0.5 | 0.54 | +0.04 |
| 0.6 | 0.58 | −0.02 |

Of course the more testing points used, the more accurate the corrective coefficient data set will be and the more useful the resulting output signal will be at reading pressures at the implanted testing site within the patient. It is preferred that rather than establishing one corrective coefficient per testing point, a polynomial function p is established having degree n that satisfies following equation:

P-ref=$p$(Sensor-Raw-Data(P-ref,T-ref))

As is well known by those skilled in the art, function p can be established by performing curve fitting techniques from the testing points. The resulting number of calibration coefficients will be (n+1). For example, a polynomial function p has a degree 3 and is satisfied using four calibration coefficients a, b, c, d to describe the function $y=a*x^3+b*x^2+c*x+d$]

The conventional implant used in the above-described calibration process includes a bidirectional RF communication link to both transmit sensor-raw data to the remote controller/reader and also to receive calibration coefficients from the remote controller/reader to store in its memory. As described in the background section of this application, one of the two-way RF links is used only during calibration and thereafter remains trapped within the implant as a "dead" component. In contrast, according to the present invention, the present implant uses a unidirectional RF communication link between the implant and the remote controller/reader to transmit sensor-raw data to the remote controller/reader, and an optical communication link to receive either the calibration coefficients or the accepted from the remote controller/reader to store in its memory.

According to the present invention, the calibration process includes the following steps:

A) The non-calibrated encapsulated sensor is "characterized", wherein the implant (with its encapsulated sensor) is placed within a pressure-controlled and temperature-controlled hermetic chamber.

B) The implant is then interrogated wirelessly by a remote control unit. The implant detects the RF energy and converts the energy to help power the onboard electrical components within the implant and initiate a set of instructions stored within the memory onboard.

C) The pressure (P-ref) and temperature (T-ref) within the chamber are varied in a controlled and known manner. The onboard sensor response is continuously read as a function of the changing T-ref and P-ref and recorded during the process.

The output of this characterization step is Sensor-Raw-Data (data from the non-calibrated sensor), where Sensor-Raw-Data is a function of the pressure and temperature of the chamber for each reading:

Sensor-Raw-Data=$f$(P-ref,T-ref).

D) The implant then uses an RF communication link to transmit the sensor-raw data to the remote controller.
E) A computer based algorithm within the remote controller uses this information to compute the sensor calibration coefficients from function (f).
F) The computer uses an optical communication link to transmit the calculated calibration coefficients to the onboard circuitry in the implant, which are then stored within the onboard non-volatile memory located within the implant.

After the calibration process is complete, the optical communication component located within the implant will no longer be used. After calibration, the only communication between the implant and the outside world (the reader) will be in one direction, from the implant to the reader, and this will be done using the unidirectional RF wireless component.

One clear benefit to using an optical coupler pair (Light Emitter and light detector) to provide one-way communication across the housing barrier from external device to the implant is that the single light-detector component (a photodiode) is considerably less expensive and smaller than the electronics that would be needed for implementing bi-directional RF communication between the implant and the external device.

Figure 2:
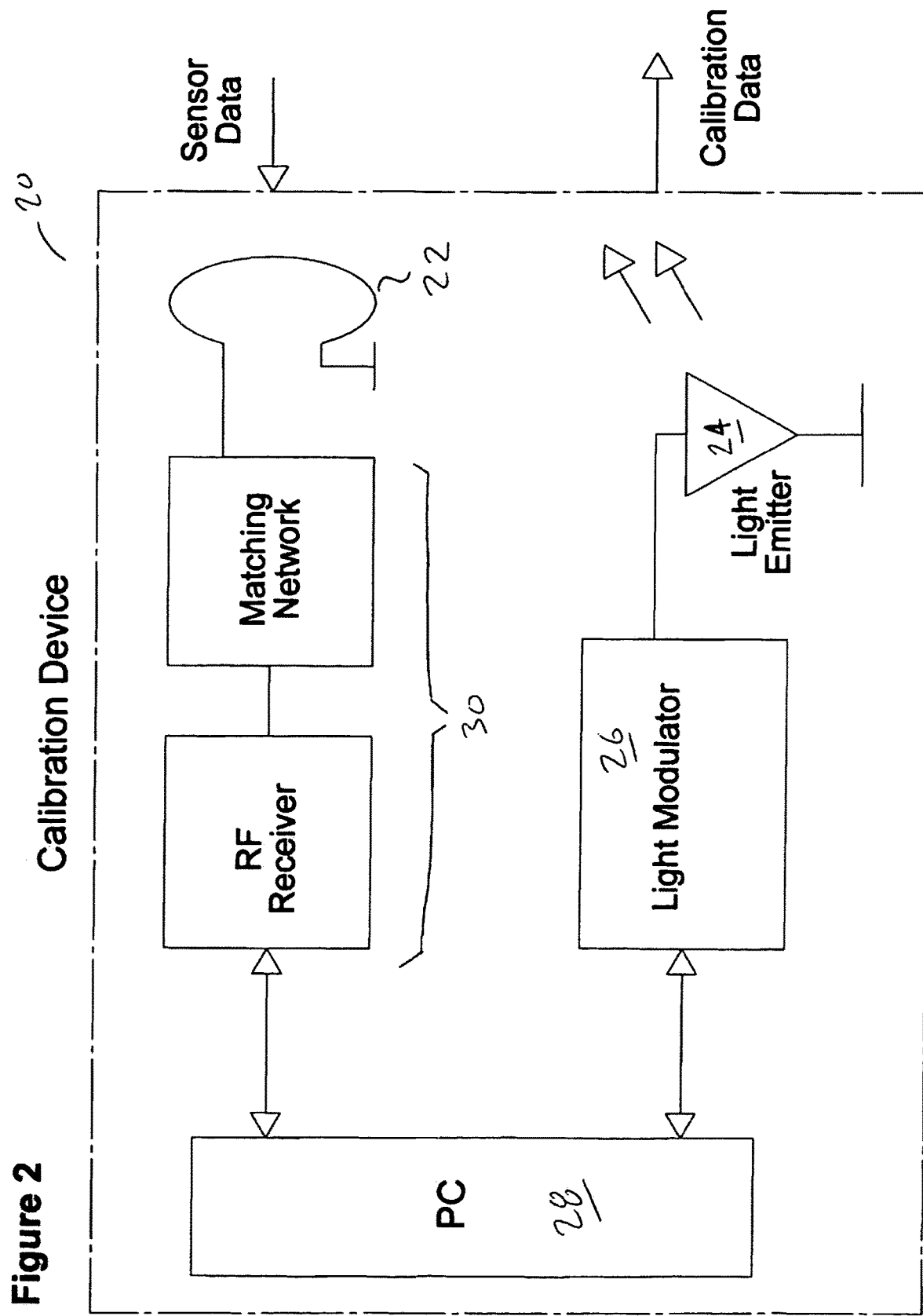
FIG. 2 is a block schematic view of the operation and connection of the calibration circuitry, including a light emitting device and a light modulation circuit, according to the invention.

Referring now to FIG. 1, an implant 10 is shown having a housing 12 made up of a cover 14 and a base plate 16. As described in greater detail below, cover 14 is hermetically secured to a top surface of base plate 16 so that an internal cavity 18 is formed. Implant housing 10 shown in the figures is used to illustrate the present invention. Of course, the present invention may be applied to an implant housing of any shape or size, including housings made from several sections. Shown below implant 10 in FIG. 1 and also referring to FIG. 2 is a calibration device 20 according to the present invention. Calibration device includes an RF loop antenna 22, a light emitter 24, an electro-optic modulation circuit 26, a microprocessor 28 and RF-communication circuitry 30.

Located within cavity 18 is an implant sensor 32 which can be any of many different sensor types depending on the particular type and application of the implant. Sensor 32 can be a thermocouple for measuring temperatures, a pressure transducer, a flow-meter for measuring the flow of a body fluid or another type. Sensor 32 can also be an actuator which provides mechanical movement, light, ultra-sonic energy, electromagnetic energy, heat energy or other when activated. The exemplary sensor 32 shown in the figures of this application is a pressure transducer. The present invention can apply to any type of sensor that is hermetically sealed within a housing and must be calibrated prior to use, or at some point in its useful lifetime.

Figure 3:
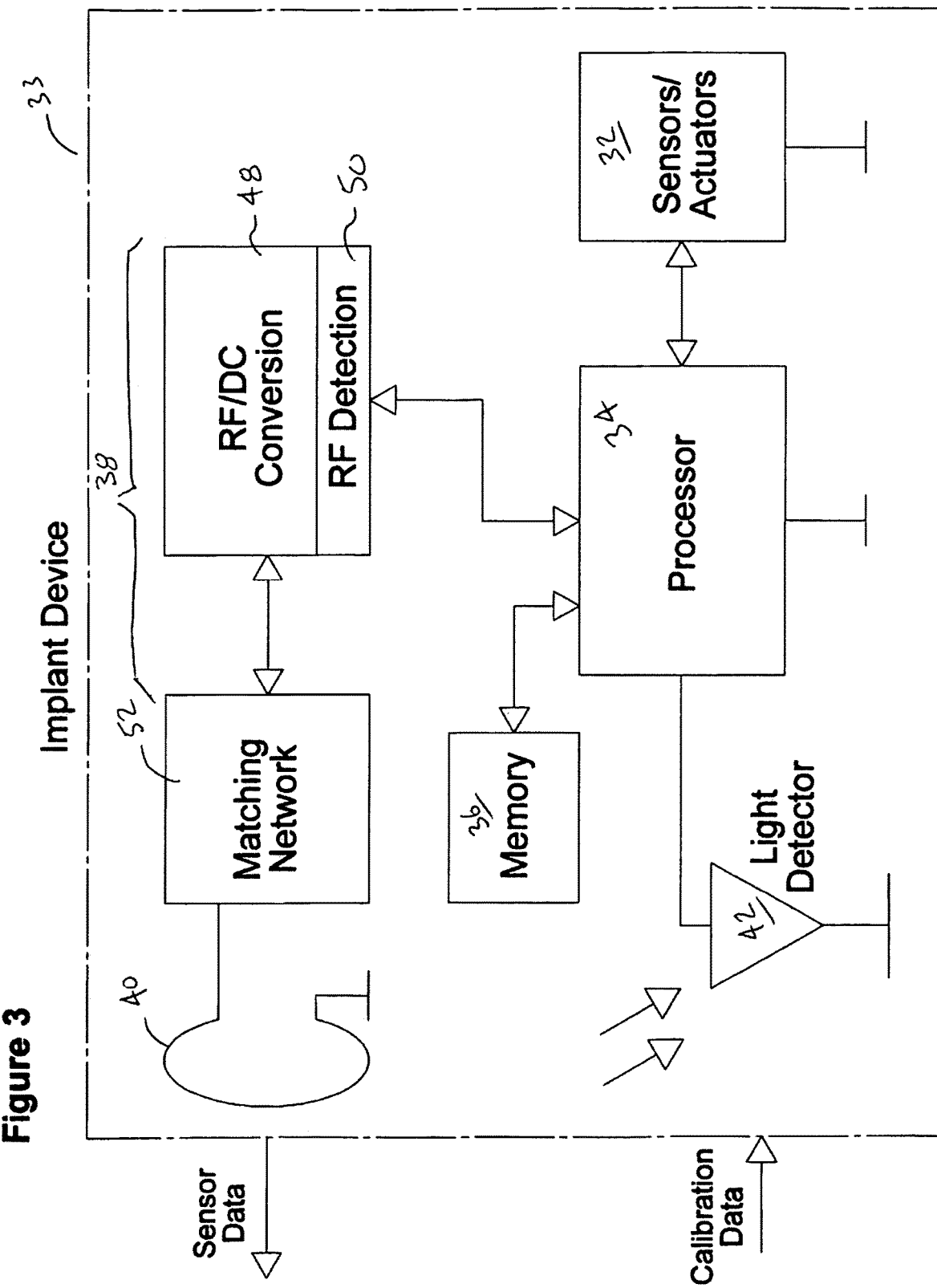
FIG. 3 is a block schematic view of the operation and connection of the onboard controlling circuitry, including communication circuitry, having a photo-sensor component, according to the invention.

Referring now to FIGS. 1 and 3, also located within cavity 18 of housing 12 is operational circuitry 33 which includes various supporting electronic components including a microprocessor 34, an electronic memory 36, RF-communication circuitry 38, a loop antenna 40, a light detector 42, and either a battery (not shown) or an induction coil 46. As described below, loop antenna 40 and induction coil 46 can use a common coil wherein RF energy received by loop antenna can be used to power the on-board circuitry.

RF-communication circuitry 38 includes an RF/DC conversion circuit 48, an RF detection circuit 50 and a matching network 52. RF/DC conversion circuit 48 is a well known circuit used to convert RF energy into DC power. Loop antenna 40 is connected to RF/DC conversion circuit 48 through matching network block 52 so that incoming RF energy does not carry data, but is used instead to as ame energy source that can be converted to a DC power supply to power the onboard electrical components. Appropriate known voltage regulation circuitry and rectifying circuitry (not shown or otherwise described) can be provided to "cleanup" this DC power so that it can be used to effectively "wakeup" and power the onboard circuitry of the implant without damaging the components.

Although considered beyond the scope of the present invention, Applicant would like to indicate that there are several known modulation schemes to both transmit data and simultaneously transmit inductive power to an implanted device from a single mated coil pair. Among these schemes are load-shift keying, phase-shift keying, frequency-shift keying and amplitude-shift keying. These and other modulation techniques are described in an article entitled: "Data Transmission from an Implantable Biotelemeter by Load-Shift Keying Using Circuit Configuration Modulator," by Zhengnian Tang, Brian Smith, John H. Schild, and P. Hunter Peckham, published in the IEEE Transaction on Biomedical Engineering, Volume 42, No. 5, May, 1995. The content of this article is hereby incorporated by reference. Such shift keying modulation allows simultaneous powering or energizing of an implanted transponder and data transmission from the transponder through the same radio frequency (RF) inductive couple. For most applications of implant devices, use of an induction coil to power the on-board components of the implant obviates the need for on-board batteries and thereby effectively extends the useful life of the present device and makes for a more compact implant assembly.

To improve the efficiency of the RF telemetry system, matching network circuit 52 is preferably provided to help tune the impedance of the transmitter with that of the receiver, as is well known by those skilled in the art. The details and component descriptions of the RF-communication circuitry 38 as well as the matching network circuitry 52 is beyond the scope of this invention and therefore not described in any great detail in the present application. For the purpose of describing the present invention, let it be understood that RF-communication circuitry 38 together with matching network circuitry 52 include the necessary components to receive an RF energy signal from a reader 60 (see FIG. 1), convert at least a portion of the RF signal to useful DC power to power the onboard electrical components and transmit a data signal as a carry signal on an RF wave back to the reader 11.

Also, although RF transmission is the preferred method for sending data from the implant to an adjacent reader, other methods can be used depending on the location and accessibility of the implanted device.

As introduced above, an important aspect of the present invention is that optical components are used to communicate with the implant during the calibration process. This requires that a portion of either base plate 16 or cover 14 which makes up the hermetically sealed housing 12 be made from a translucent or transparent material. This will allow the passage of modulated light from light emitter 24 of calibration assembly 20 through housing 12 to light detector 42 of operational circuitry 33. To this end, at least a portion of housing 12 is made from glass, transparent or translucent plastic or even an appropriate transparent or translucent mineral, such as quartz. It is preferred that the base plate be made from a borosilicate glass (such as thermal shock-resistant Pyrex® glass) so that an appropriate pressure sensor can be anodically bonded to base plate 16. Cover 14 may be any appropriate material that can be hermetically sealed to the glass base plate. As described above in the background section of this application, the borosilicate glass components used as the housing can be fused together using well known brazing techniques.

During calibration of the implant, a bidirectional wireless link is established between the implant and an external device. According to the invention, the wireless link uses an RF carrier signal to transfer data from the implant to the reader, and light for transferring data from the external calibration device and the implant. According to a first embodiment of the invention, a passive telemetry communication technique is used wherein data is transferred from the implant to the nearby reader based on load modulation (or absorption modulation) performed by the implant in response to the implant receiving RF non-modulated energy from the reader. With this arrangement, there is actually no active transmission (and therefore no active modulation or RF transmission) from the implant. Rather than active modulation, described below in a second embodiment of the invention, the implant performs "backscattering modulation" (also called "load modulation" or "absorption modulation") of the incoming RF energy to effectively transfer data from the implant to the reader. In this first embodiment, according to the invention and described above, light is used to transfer data from an external calibration device to the implant during calibration.

According to a second embodiment, implant 10 includes two antennas as part of an active telemetry system. Here, a first antenna is used to collect energy from the external reader through inductive coupling (a well known and understood technique), and a second antenna is connected to an active RF transmitter and is used to emit a modulated RF signal from the implant back to the reader. Again, light is used to transfer data from the external calibration device to the implant during calibration.

The light is generated by the light emitter 24 and is preferably a laser diode, but may also be an appropriate LED. The emitted light is modulated by electro-optical modulation circuit 26 so that data may be transmitted to the implant by pulsating the emitted light. The modulation may be imposed on the phase, frequency, amplitude, or direction of the modulated beam. Modulation bandwidths extending into the gigahertz range are possible with the use of laser-controlled modulators.

By selecting a unique wavelength and intensity of the light generated by emitter 24, the risk that sensor 32 will accidentally become reprogrammed after implantation by stray light is mitigated. This risk would actually be higher with a standard telemetric link, since the implant would be in this case exposed to a variety of sources of RF waves, for example MRIs, security gates, mobile phones, industrial electromagnetic environment, etc. Conventional implants that use RF to calibrate might therefore become accidentally reprogrammed if the implant software does not include relatively complicated security measures for preventing such accidental reprogramming. In contrast, owing to the inherent security of an optical link, an implant of the present invention does not require complicated operation software and may be considerably simplified.

A bore 54, shown in FIG. 1 is formed within a portion of housing 12 (preferably through base plate 16) so that pressure transducer (sensor 32) may read the pressure of the environment located outside housing 12 of implant 10, as required. If the implant is a brain implant, then the cerebrospinal fluid (CSF) located within the patient's skull is allowed to enter bore 54 and interact directly with pressure transducer 32, as necessary, but is otherwise sealed from the other components within housing 12 using appropriate well known sealing techniques, such as anodic bonding.

In operation, after implant 10 has been properly calibrated and is implanted within a patient, an appropriate reader 60 having an antenna 62, may be used to both "wake up", power, and extract sensor data in real time from the implant 10. When the RF energy from reader 60 reaches loop antenna 40 of implant 10, the RF energy is converted to a DC power supply to power the onboard components, as described above, using RF/DC conversion circuitry 38. An RF detection circuit 50 detects the incoming interrogation RF signal and initiates processor 34 to follow the instructions of prescribed program located in non-volatile memory 36. This program automatically causes processor 34 to read the output of sensor 32 and to use the calibration coefficients stored in memory 36 to calculate a calibrated sensor-data set. Processor 34 then transmits this adjusted or calibrated sensor data (e.g., a pressure value) to the external reader using RF communication circuitry 38 to be transmitted as a carrier signal on a generated RF energy wave back to the awaiting reader 60 (picked up by antenna 62) located outside the patient's body.

Operational circuitry of implant 10 will typically include other components such as analog to digital conditioning circuitry (not shown) to help modify the output signals from sensor 32 to a form that can be handled and transmitted more efficiently and more reliably. Also, an oscillator circuit (not shown) may be included, connected to the processor provide a clocking signal that is necessary for the processor to operate. Furthermore, appropriate circuitry (not shown) for multiplexing and encrypting the data as a carrier signal on an RF wave prior to transmission are all well known techniques by those skilled in the art, the circuitry details required to accomplish these tasks are not described here in any great detail.

Loop antenna 40 of implant 10 is preferably formed from a coil of conductive material such as metallic wire, carbon fiber wires, conductive ink, conductive elastomeric materials, or other conventional inductor materials.

Although an exemplary embodiment of the present invention has been shown and described, it will be apparent to those having ordinary skill in the art that a number of changes, modifications, improvements, or alterations to the invention as described herein may be made, none of which depart from the spirit of the present invention. All such changes, modifications, and alterations should therefore be seen as within the scope of the present invention. Accordingly, no limitation on the invention is intended by way of the foregoing description and the accompanying drawings, except as set forth in the appended claims.

What is claimed is:

1. A method for calibrating a sensor of an implant before implantation into a body and using the sensor and the implant in the body, wherein said sensor is connected to control circuitry which includes a processor, a radio frequency (RF) communication circuitry, optical communication circuitry including a light-receiving device, a power source and memory, all of which being hermetically sealed within a housing, the sensor is disposed on a base plate, said method comprising the steps of:

creating a bore through the base plate;

placing the sensor over the bore so that the sensor is exposed to an external atmosphere while being hermetically sealed within the housing;

placing said implant into a controlled environment outside of the body;

creating an RF communication link between a remote controller and said RF communication circuitry of said control circuitry, whereby the control circuitry converts RF energy from the remote controller to help power at least the processor and RF communication circuitry;

adjusting at least one aspect of said controlled environment to a first known value;

allowing said sensor to measure said at least one aspect of said controlled environment and generate a first sensor reading;

transmitting said first sensor reading from said implant to said remote controller using said RF communication link;

comparing said received first sensor reading with said first known value of said at least one aspect of said controlled environment to create a first corrective coefficient;

creating an optical communication link between said remote controller and said control circuitry of said implant before implantation into the body;

transmitting said first corrective coefficient to said memory of said control circuitry using said optical communication link;

allowing said control circuitry of said implant to use said first corrective coefficient to adjust said first sensor reading to align with said first known value for future readings;

implanting said sensor and said implant within said body; and transmitting, after calibration and implantation, RF energy from said remote controller to said implant in said body for activating said sensor, powering at least said processor and said RF communication circuitry of said sensor to read output of said sensor and use the first corrective coefficient to calculate calibrated sensor data, and extracting calibrated sensor data in real time from said sensor implanted in said body.

2. The method for calibrating according to claim 1, wherein said at least one aspect is selected from the list of pressure, temperature, humidity, acidity, oxygen, glucose and flow rate.

3. The method for calibrating according to claim 1, wherein said housing includes a transparent region through which said optical communication may occur.

4. The method for calibrating according to claim 3, wherein said base plate is made from glass.

5. The method for calibrating according to claim 3, wherein said base plate is made from a glass that is suitable for anodic bonding.

6. The method for calibrating according to claim 3, wherein said step of transmitting said first corrective coefficient to said memory of said control circuitry using said optical communication link includes modulating a light emitter outside said housing so that modulated light can pass through said transparent region and be received by said light receiving device and demodulated by said control circuitry.

7. The method for calibrating according to claim 6, wherein said housing includes at least one part made from glass.

8. The method for calibrating according to claim 7, wherein said glass part is made from a glass that is appropriate for anodic bonding.

9. The method for calibrating according to claim 6, wherein said light receiving device is a photo-detector.

10. The method for calibrating according to claim 9, wherein said photo-detector is either a phototransistor or a photodiode.

11. The method for calibrating according to claim 1, wherein said RF communication link and said optical communication link operate simultaneously.

12. The method for calibrating according to claim 1, wherein said light-receiving device comprises a photo-detector, wherein said photo-detector is either a phototransistor or a photodiode.

13. A method for calibrating a pressure sensor of an implant before implantation into a body wherein said sensor is connected to control circuitry which includes a processor, a radio frequency (RF) communication circuitry, optical communication circuitry including a photo-detector, a power source and memory, all of which being hermetically sealed within a housing having a transparent window, the sensor is disposed on a base plate, said method for calibrating comprising the steps of:

creating a bore through the base plate;

placing the sensor over the bore so that the sensor is exposed to an external atmosphere while being hermetically sealed within the housing;

placing said implant into a pressure chamber outside of the body;

creating an RF communication link between a remote controller and said RF communication circuitry of said control circuitry, whereby the control circuitry converts RF energy from the remote controller to help power at least the processor and RF communication circuitry;

adjusting the pressure within said chamber to a known first pressure value;

allowing said sensor to measure said known first pressure of said chamber and generate a first sensor pressure reading;

transmitting said first sensor pressure reading from said implant to said remote controller using said RF communication link;

comparing said received first sensor pressure reading with said known first pressure value to create a first corrective coefficient;

creating an optical communication link between said remote controller and said control circuitry of said implant through said transparent window before implantation into the body;

transmitting said first corrective coefficient to said memory of said control circuitry using said optical communication link;

allowing said control circuitry to use said first corrective coefficient to adjust said first sensor pressure reading to align with said known first pressure reading for future readings;

implanting said sensor and said implant within said body; and transmitting, after calibration and implantation within said body, RF energy from said remote controller to said implant in said body for activating said sensor, powering at least said processor and said RF communication circuitry of said sensor to read output of said sensor and use the first corrective coefficient to calculate calibrated sensor data, and extracting calibrated sensor data in real time from said sensor implanted in said body.

14. The method for calibrating according to claim 13, wherein said step of transmitting said first corrective coefficient to said memory of said control circuitry using said optical communication link includes modulating a light emitter outside said housing so that modulated light can pass through said transparent window and be received by said photodiode and demodulated by said control circuitry.

15. The method for calibrating according to claim 13, wherein said base plate is made from glass.

16. The method for calibrating according to claim 15, wherein said base plate is made from a glass that is suitable for anodic bonding.

* * * * *